United States Patent
Kume et al.

(10) Patent No.: US 10,464,430 B2
(45) Date of Patent: Nov. 5, 2019

(54) POWER RECEPTION APPARATUS, VEHICLE, AND DETECTION METHOD

(71) Applicant: HONDA MOTOR CO., LTD., Tokyo (JP)

(72) Inventors: Yasuhisa Kume, Wako (JP); Tomoaki Ono, Wako (JP); Takuya Iwamoto, Wako (JP); Hajime Fujita, Tokyo (JP)

(73) Assignee: HONDA MOTOR CO., LTD., Tokyo (JP)

( * ) Notice: Subject to any disclaimer, the term of this patent is extended or adjusted under 35 U.S.C. 154(b) by 124 days.

(21) Appl. No.: 15/630,280

(22) Filed: Jun. 22, 2017

(65) Prior Publication Data

US 2017/0368946 A1 Dec. 28, 2017

(30) Foreign Application Priority Data

Jun. 27, 2016 (JP) .................................. 2016-126443

(51) Int. Cl.

| | |
|---|---|
| *B60L 53/12* | (2019.01) |
| *H02J 50/10* | (2016.01) |
| *H02J 50/80* | (2016.01) |
| *H02J 7/00* | (2006.01) |
| *G01N 27/00* | (2006.01) |
| *G01P 15/00* | (2006.01) |
| *H01F 27/02* | (2006.01) |
| *H01F 27/40* | (2006.01) |
| *H01F 38/14* | (2006.01) |
| *B60L 11/18* | (2006.01) |

(52) U.S. Cl.
CPC ............. *B60L 11/182* (2013.01); *B60L 53/12* (2019.02); *G01N 27/00* (2013.01); *G01P 15/001* (2013.01); *H01F 27/02* (2013.01); *H01F 27/025* (2013.01); *H01F 27/402* (2013.01); *H01F 38/14* (2013.01); *H02J 50/10* (2016.02)

(58) Field of Classification Search
CPC ......... B60L 11/182; B60L 53/12; H02J 50/10; H02J 50/80; H02J 7/0013; G01N 27/00; G01P 15/001; H01F 27/02; H01F 27/025; H01F 27/402; H01F 38/14; Y02T 10/7055

See application file for complete search history.

(56) References Cited

FOREIGN PATENT DOCUMENTS

| | | |
|---|---|---|
| JP | 2015-65720 A | 4/2015 |
| WO | 2015/045246 A1 | 4/2015 |

*Primary Examiner* — Hal Kaplan
(74) *Attorney, Agent, or Firm* — Westerman, Hattori, Daniels & Adrian, LLP

(57) ABSTRACT

A power reception apparatus includes a secondary coil which receives power in a non-contact state from a power transmission apparatus having a primary coil, while being disposed opposite to the power transmission apparatus, a housing which accommodates the secondary coil to form a space between the secondary coil and the housing, an insulating fluid filled in the space, a measurement unit which measures efficiency of a non-contact power transmission between the primary coil and the secondary coil, and a detection unit which detects damage made to the housing based on a change in the efficiency during the non-contact power transmission.

18 Claims, 7 Drawing Sheets

POWER RECEPTION APPARATUS, VEHICLE, AND DETECTION METHOD

CROSS-REFERENCE TO RELATED APPLICATION

This application claims priority from Japanese Patent Application No. 2016-126443 filed on Jun. 27, 2016, the entire contents of which are incorporated herein by reference.

TECHNICAL FIELD

The present invention relates to a power reception apparatus, a vehicle, and a detection method that utilize a non-contact power transmission technology.

BACKGROUND ART

The industry has been focusing on the non-contact power transmission technology that takes the usability in charging into consideration as a technology for charging a battery installed on a vehicle such as a hybrid electric vehicle or an electric vehicle that is driven by an electric motor. Patent literature 1 describes a vehicle including a power reception apparatus that utilizes the non-contact power transmission technology. This power reception apparatus has a construction in which a coil and a core unit are sealed up by a resin member, and heat generated from the coil and the core unit can be radiated to the outside through the resin member.

RELATED ART LITERATURE

Patent Literature

Patent Literature 1: JP-A-2015-65720

SUMMARY OF THE INVENTION

Problem that the Invention is to Solve

The power reception apparatus of patent literature 1 described above is fixed to a floor panel that constitutes a bottom surface of a vehicle body with bolts, and therefore, there is a risk of the resin member that seals up the coil and the core unit therein being subjected to an impact from an exterior portion to be damaged. The damage of the resin member is not preferable because it possibly triggers a problem that the heat radiating performance is reduced or the receiving efficiency is reduced in association with a change in impedance. In the power reception apparatus of patent literature 1, however, no means for detecting damage of the resin member is disclosed or implied.

An object of the present invention is to provide a power reception apparatus, a vehicle, and a detection method capable of realizing cooling of a secondary coil and a detection of damage made to a housing by the use of a simple and easy configuration.

Means for Solving the Problem

In order to achieve the above object, according to aspect 1 of the present invention, there is provided a power reception apparatus including:

a secondary coil (for example, a secondary coil 31) which receives power in a non-contact state from a power transmission apparatus (for example, a power transmission apparatus T) having a primary coil (for example, a primary coil L), while being disposed opposite to the power transmission apparatus;

a housing (for example, a housing 32) which accommodates the secondary coil to form a space (for example, a space S) between the secondary coil and the housing;

an insulating fluid (for example, an insulating fluid F) filled in the space:

a measurement unit (for example, a measurement unit 34) which measures efficiency of a non-contact power transmission between the primary coil and the secondary coil; and a detection unit (for example, a detection unit 37) which detects damage made to the housing based on a change in the efficiency during the non-contact power transmission.

According to aspect 2 of the present invention, there is provided a power reception apparatus including:

a secondary coil (for example, the secondary coil 31) which receives power in a non-contact state from a power transmission apparatus (for example, the power transmission apparatus T) having a primary coil (for example, the primary coil L), while being disposed opposite to the power transmission apparatus;

a housing (for example, the housing 32) which accommodates the secondary coil to form a space (for example, the space S) between the secondary coil and the housing;

an insulating fluid (for example, the insulating fluid F) filled in the space;

a measurement unit (for example, the measurement unit 34) which measures a coupling coefficient between the primary coil and the secondary coil; and a detection unit (for example, the detection unit 37) which detects damage made to the housing based on a change in the coupling coefficient between at a first time and at a second time that has elapsed from the first time.

According to aspects 3 and 4 of the present invention, the power reception apparatus includes a sensor (for example, an acceleration sensor 38) which detects an impact against the power reception apparatus, and the detection unit detects damage made to the housing in a case that the sensor detects no impact during the non-contact power transmission, and a change in the efficiency or a change in the coupling coefficient during the non-contact power transmission is a reduction of a predetermined value or greater.

According to aspects 5 and 6 of the present invention, the power reception apparatus includes an acquisition unit (for example, a communication unit 33) which acquires information related to a power change of an exterior power system to which the primary coil is connected, and the detection unit detects damage made to the housing in a case that the information does not indicate a power change of the power system during the non-contact power transmission, and a change in the efficiency or the coupling coefficient during the non-contact power transmission is a reduction of a predetermined value or greater.

According to aspects 7 and 8 of the present invention, the power reception apparatus includes:

a sensor (for example, the acceleration sensor 38) which detects an impact against the power reception apparatus; and an acquisition unit (for example, the communication unit 33) which acquires information on a power change of an exterior power system to which the primary coil is connected, and the detection unit detects damage made to the housing in case that the sensor detects no impact during the non-contact power transmission, the information does not indicate a power change of the power system during the non-contact power transmission, and a change in the efficiency or the coupling coefficient during the non-contact power transmission is a reduction of a predetermined value or greater.

According to aspects 9 and 10 of the present invention, the housing includes a support portion (for example, a base plate 32a) which supports the secondary coil, and the support portion has a higher heat conductivity than that of the secondary coil.

According to aspects 11 and 12 of the present invention, the support portion has a higher heat conductivity than that of the insulating fluid.

According to aspects 13 and 14 of the present invention, the power reception apparatus includes a transmission unit (for example, the communication unit 33) which transmits a command to stop power transmission of to the secondary coil in a case that the detection unit detects damage made to the housing.

According to aspects 15 and 16 of the present invention, there is provided a vehicle having the above power reception apparatus.

According to aspect 17 of the present invention, there is provided a detection method that is executed by a power reception apparatus including:

a secondary coil (for example, a secondary coil 31) which receives power in a non-contact state from a power transmission apparatus (for example, a power transmission apparatus T) having a primary coil (for example, a primary coil L), while being disposed opposite to the power transmission apparatus;

a housing (for example, a housing 32) which accommodates the secondary coil to form a space (for example, a space S) between the secondary coil and the housing; and an insulating fluid (for example, an insulating fluid F) filled in the space;

the method includes the steps of:

measuring efficiency of a non-contact power transmission between the primary coil and the secondary coil; and detecting damage made to the housing based on a change in the efficiency during the non-contact power transmission.

According to aspect 18 of the present invention, there is provided a detection method that is executed by a power reception apparatus including:

a secondary coil (for example, the secondary coil 31) which receives power in a non-contact state from a power transmission apparatus (for example, the power transmission apparatus T) having a primary coil (for example, the primary coil L), while being disposed opposite to the power transmission apparatus;

a housing (for example, the housing 32) which accommodates the secondary coil to form a space (for example, the space S) between the secondary coil and the housing; and an insulating fluid (for example, the insulating fluid F) filled in the space;

the method includes the steps of:

measuring a coupling coefficient between the primary coil and the secondary coil; and detecting damage made to the housing based on a change in the coupling coefficient between at a first time and at a second time that has elapsed from the first time.

Advantages of the Invention

According to aspects 1, 15, 16 and 17 of the present invention, since the insulating fluid is filled in the space within the housing where the secondary coil is accommodated, the secondary coil can be cooled through convection of the insulating fluid. When the housing is damaged, since the insulating fluid leaks from damaged portion or bubbles of air enter an interior of the space from the damaged portion, a magnetic permeability around the secondary coil changes to change the efficiency of non-contact power transmission between the primary coil and the secondary coil. According to the measurement unit or the measurement step for measuring the efficiency, it is possible to detect damage to the housing from a change in the efficiency. In this way, according to aspects 1, 9 and 10 of the present invention, the cooling of the secondary coil and the detection of damage made to the housing can be realized at low cost by the simple and easy configuration.

According to aspects 2, 15, 16 and 18 of the present invention, since the insulating fluid is filled in the space within the housing where the secondary coil is accommodated, the secondary coil can be cooled through convection of the insulating fluid. When the housing is damaged, since the insulating fluid leaks from a damaged portion or bubbles of air enter an interior of the space from the damaged portion, a magnetic permeability around the secondary coil changes. As a result, the coupling coefficient between the primary coil and the secondary coil changes. According to the measurement unit or the measurement step for measuring the coupling coefficient, it is possible to detect damage to the housing from a change in the coupling coefficient. In this way, according to aspects 2, 9 and 11 of the present invention, the cooling of the secondary coil and the detection of damage made to the housing can be realized at low cost by the simple and easy configuration.

According to aspects 3 and 4 of the present invention, even though there occurs a change in the efficiency of the non-contact power transmission between the primary coil and the secondary coil or a change in the coupling coefficient between the primary coil and the secondary coil due to an impact being applied to the power reception apparatus, since there is caused no erroneous detection of damage made to the housing, it is possible to improve the accuracy with which damage to the housing is detected.

According to aspects 5 and 6 of the present invention, even though there occurs a change in the efficiency of the non-contact power transmission between the primary coil and the secondary coil or a change in the coupling coefficient between the primary coil and the secondary coil due to a power change of the power system during the non-contact power transmission, since there is caused no erroneous detection of damage made to the housing, it is possible to improve the accuracy with which damage to the housing is detected. The power change of the power system including, for example, a frequency change and a voltage drop, and both the frequency change and the voltage drop deteriorate the impedance matching or reduces the transmission amount of power, thereby affecting badly the efficiency of the non-contact power transmission.

According to aspects 7 and 8 of the present invention, even though there is influence imposed by a change in the efficiency of the non-contact power transmission between the primary coil and the secondary coil or a change in the coupling coefficient between the primary coil and the secondary coil due to an impact against the power reception apparatus or a power change of the power system during the non-contact power transmission, since there is caused no erroneous detection of damage made to the housing, it is possible to improve the accuracy with which damage to the housing is detected.

According to aspects 9 and 10 of the present invention, heat generated by the secondary coil can be radiated to an exterior portion by way of the support portion.

According to aspects 11 and 12 of the present invention, heat that has reached from the secondary coil to the insulating fluid can be radiated to an exterior portion by way of the support portion.

According to aspects 13 and 14 of the present invention, since the transmission of power to the secondary coil is stopped when damage to the housing is detected, it is possible to improve the safety.

MODE FOR CARRYING OUT THE INVENTION

Figure 1:
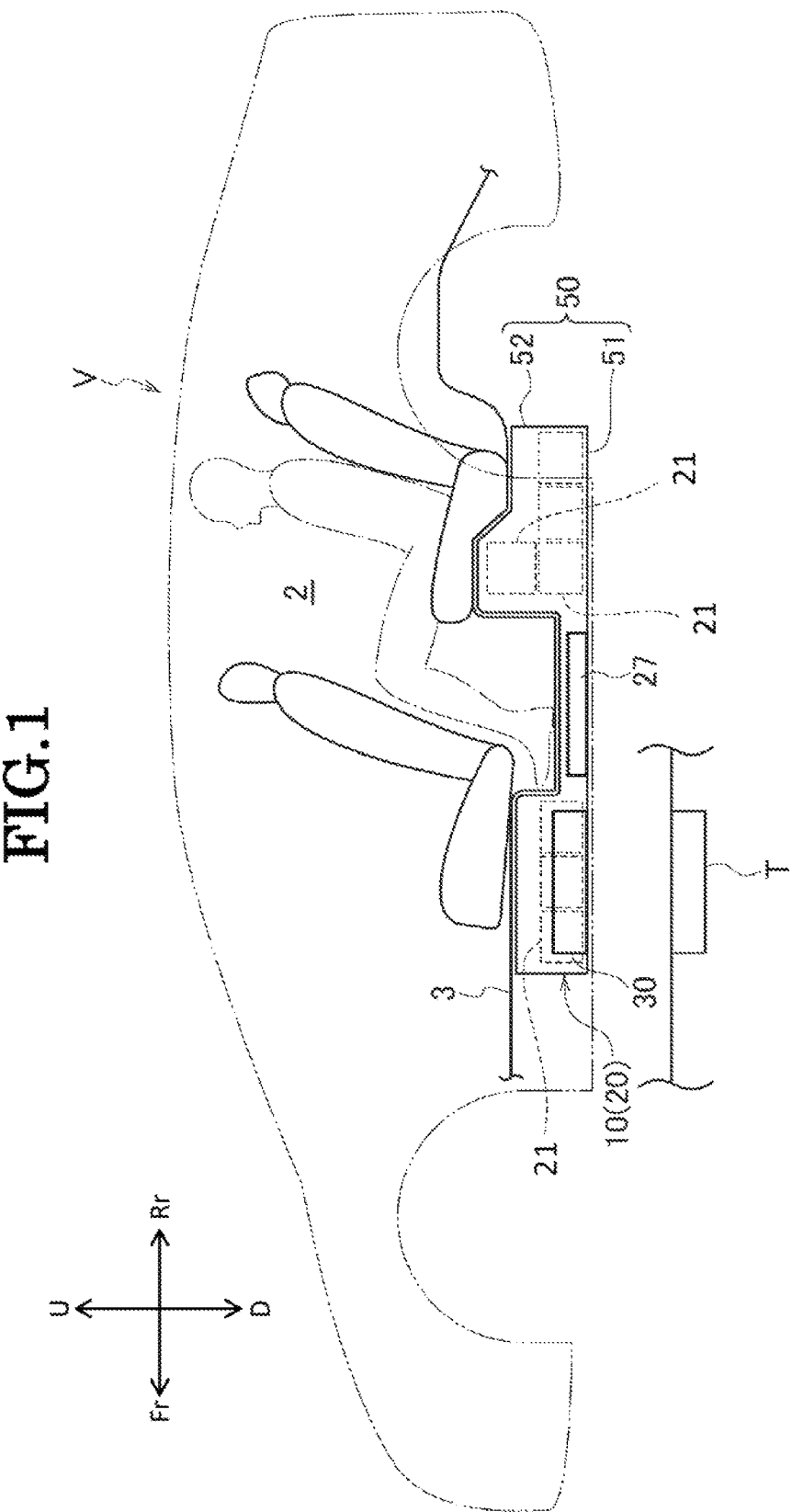
FIG. 1 is a schematic side view of a vehicle on which a power supply device is mounted which includes a power reception apparatus according to an embodiment of the invention.

Hereinafter, an embodiment of the invention will be described by reference to the drawings. The drawings should be seen in a direction in which given reference numerals look normal. In the following description, front, rear, left, right, up and down denote, respectively, such directions as seen from a driver of a vehicle, and front, rear, left, right, up and down sides of the vehicle are denoted by Fr, Rr, L, R, U and D, respectively.

As shown in FIG. 1, a power supply device 10 includes a battery unit 20 that accommodates therein a plurality of battery modules 21, a power reception apparatus 30 for receiving alternating current power in a non-contact state from a power transmission apparatus T, and a rectifier (not shown) for converting alternating current power received by the power reception apparatus 30 to a direct current and is installed on a vehicle V such as a hybrid electric vehicle, an electric vehicle, and a fuel cell vehicle. The vehicle V includes a floor panel 3 that makes up a floor surface of a passenger compartment 2, and the power supply device 10 is disposed underneath the floor panel 3, that is, at a bottom portion of the vehicle V.

The battery unit 20 includes mainly the plurality of battery modules 21, a junction box 27 and a battery case 50 for accommodating the battery modules 21 and the junction box 27.

The battery case 50 is made up of a bottom plate 51 on which the plurality of battery modules 21 and the junction box 27 are mounted and a cover 52 for covering the battery modules 21 and the junction box 27 from thereabove. At least the bottom plate 51 of the battery case 50 is formed from a material having heat conducting properties and magnetism shielding properties. In addition, the battery case 50 is attached so that the battery unit 20 is suspended below the floor panel 3 by a plurality of brackets (not shown) that extend in a left-right direction being fastened to floor frames (not shown) that are provided on both sides of the vehicle V.

The junction box 27 is a box body for accommodating a plurality of terminals that are used to connect, divide and relay conductors and safety devices such as fuses and circuit breakers.

Figure 2:
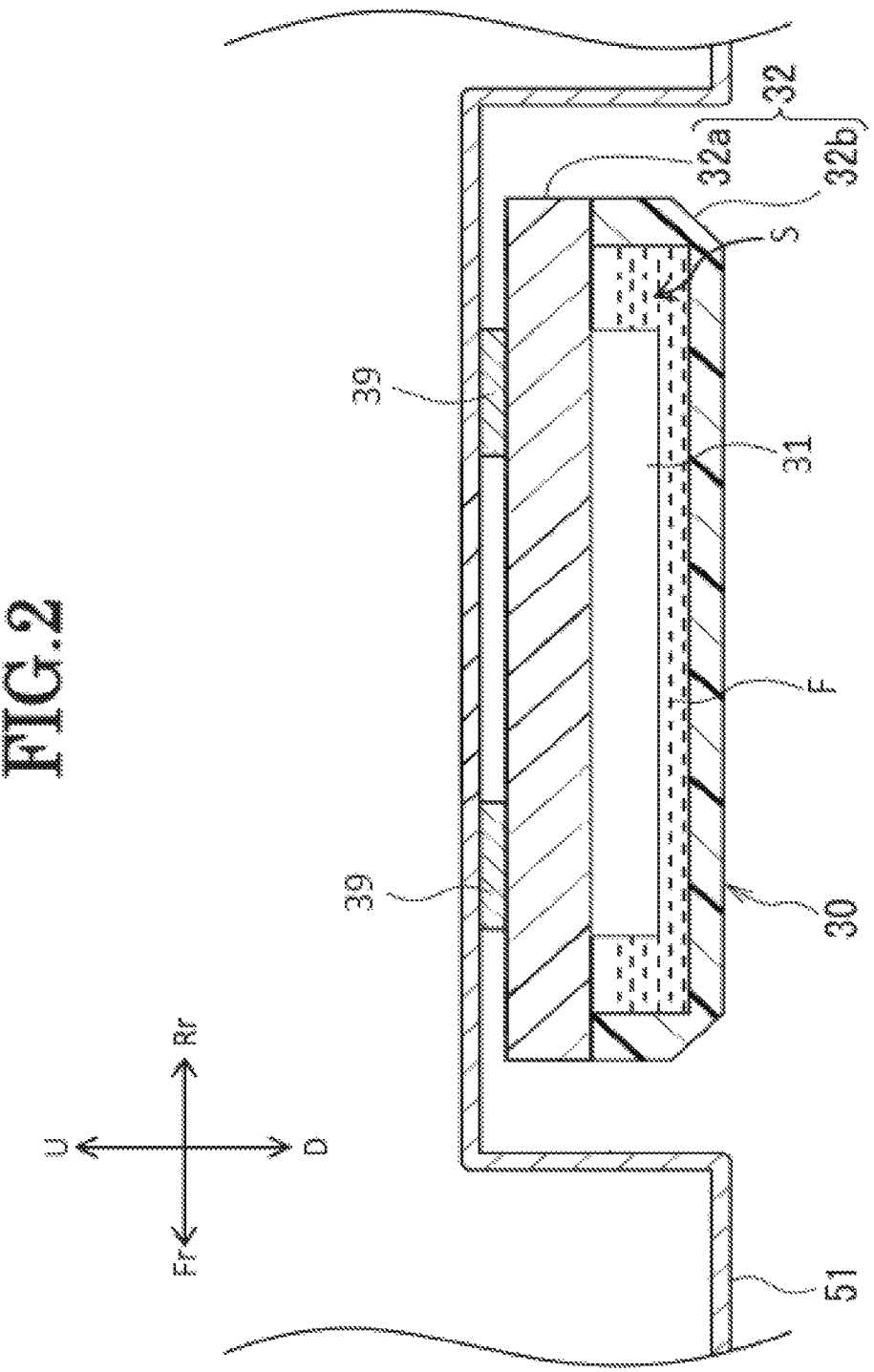
FIG. 2 is a sectional view of the power reception apparatus according to the embodiment of the invention as seen from a side thereof.
Figure 3:
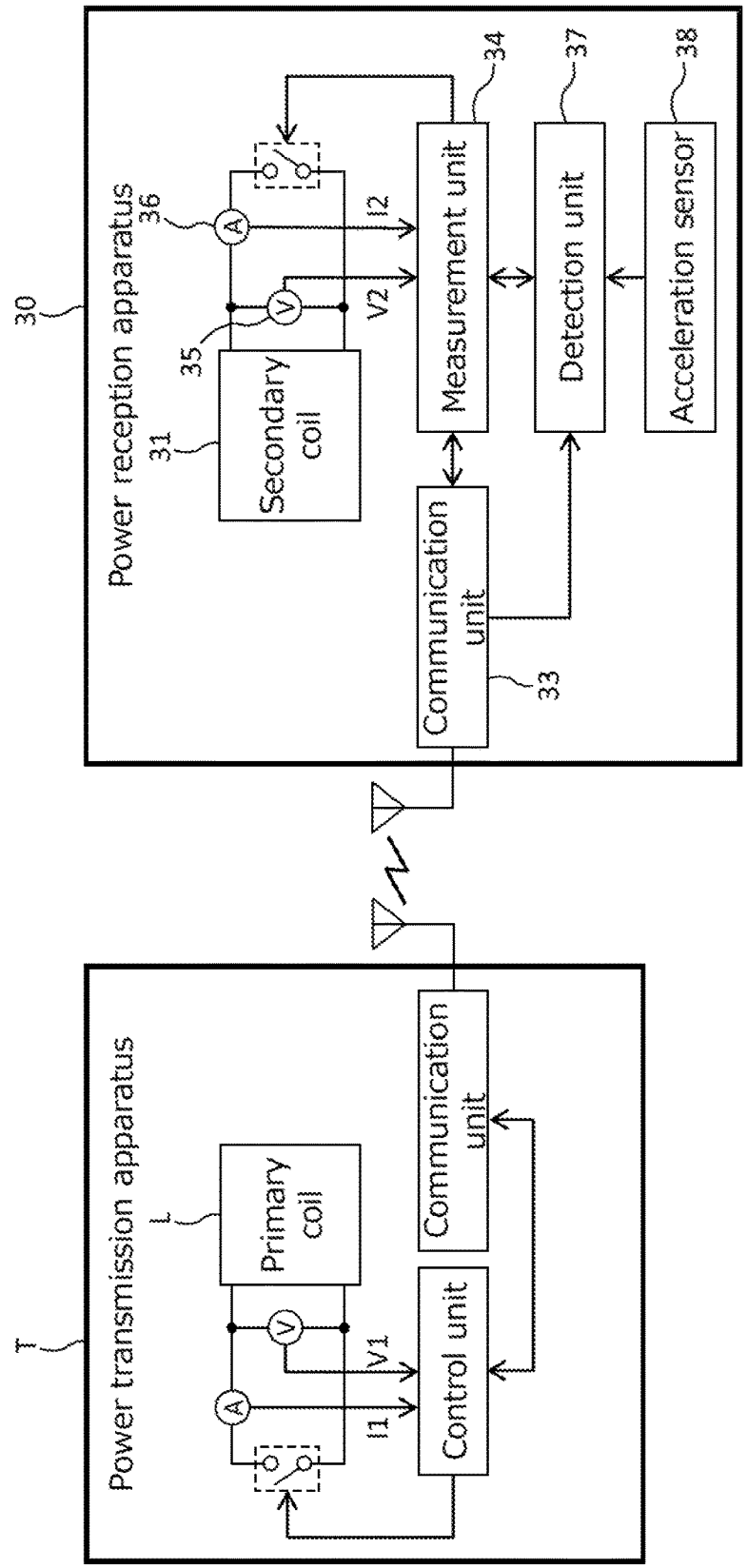
FIG. 3 is a block diagram showing interior configurations of a power transmission apparatus and the power reception apparatus.

The power reception apparatus 30 is disposed at a bottom portion of the power supply device 10 and at a bottom portion of the vehicle V and receives alternating current power that is sent by way of a primary coil of the power transmission apparatus T that is connected to an exterior power system by utilizing the non-contact power transmission technology. As shown in FIGS. 2 and 3, the power reception apparatus 30 includes a secondary coil 31, a housing 32 for accommodating the secondary coil 31 therein to form a space S between the secondary coil 31 and the housing 32, a communication unit 33, a measurement unit 34, a voltage sensor 35, a current sensor 36 and a detection unit 37, and an insulating fluid F is filled in the space S.

The secondary coil 31 is a coil for receiving power in a non-contact state from the power transmission apparatus T. When the primary coil L is excited with an alternating current with the power reception apparatus 30 disposed opposite to the power transmission apparatus T, an alternating current flows through the secondary coil 31 by means of the action of electromagnetic induction.

The housing 32 is made up or a base plate 32a that supports the secondary coil 31 and a resin cover 32b that covers the secondary coil 31 from therebelow. The base plate 32a is formed by using a material having a higher heat conductivity than that of the secondary coil 31 or the insulating fluid F such as aluminum.

The communication unit 33 receives a radio signal including information from the power transmission apparatus T and transmits a radio signal indicating a request or an instruction from the receiving unit 30 to the power transmission apparatus T.

The measurement unit 34 measures efficiency of a non-contact power transmission (hereinafter, referred to as a "transmission efficiency") between the primary coil L of the power transmission apparatus T and the secondary coil 31. The transmission efficiency is measured or obtained by a ratio (=P2/P1) of a power P2 that is obtained by multiplying a voltage V2 of the secondary coil 31 that is generated in the secondary coil 31 of the power reception apparatus 30 by a current I2 that flows through the secondary coil 31 during a non-contact power transmission to a power P1 of the primary coil L that is obtained by multiplying a voltage V1 that is applied to the primary coil L of the power transmission apparatus T by a current I1 that flows through the primary coil L during the non-contact power transmission. Consequently, the measurement unit 34 acquires information on the power P1 of the primary coil L of the power transmission apparatus T during the non-contact power transmission by way of the communication unit 33 and then acquires the voltage value V2 that is detected by the voltage sensor 35 of the power reception apparatus 30 and the current value I2 that is detected by the current sensor 36 for calculation of a transmission efficiency.

The measurement unit 34 may measure a coupling coefficient between the primary coil L and the secondary coil 31 instead of measuring the non-contact power transmission efficiency. In measuring the coupling coefficient, firstly, the measurement unit 34 measures a self-inductance Lopen(t0) of one (for example, the secondary coil 31) of the primary coil L and the secondary coil 31 at a time t0 when both the coils are open. Next, the measurement unit 34 instructs the power transmission apparatus T by way of the communication unit 33 to short-circuit the other coil (for example, the primary coil L) and then measures a leak inductance Lsc(t1) of the coil (the secondary coil 31) at a time t1 with the other coil left short-circuited. Next, the measurement unit 34 calculates a coupling coefficient k between the primary coil L and the secondary coil 31 from a mathematical equation (1) below.

$$k = \sqrt{1 - \frac{Lsc(t1)}{Lopen(t0)}} \qquad (1)$$

Figure 4:
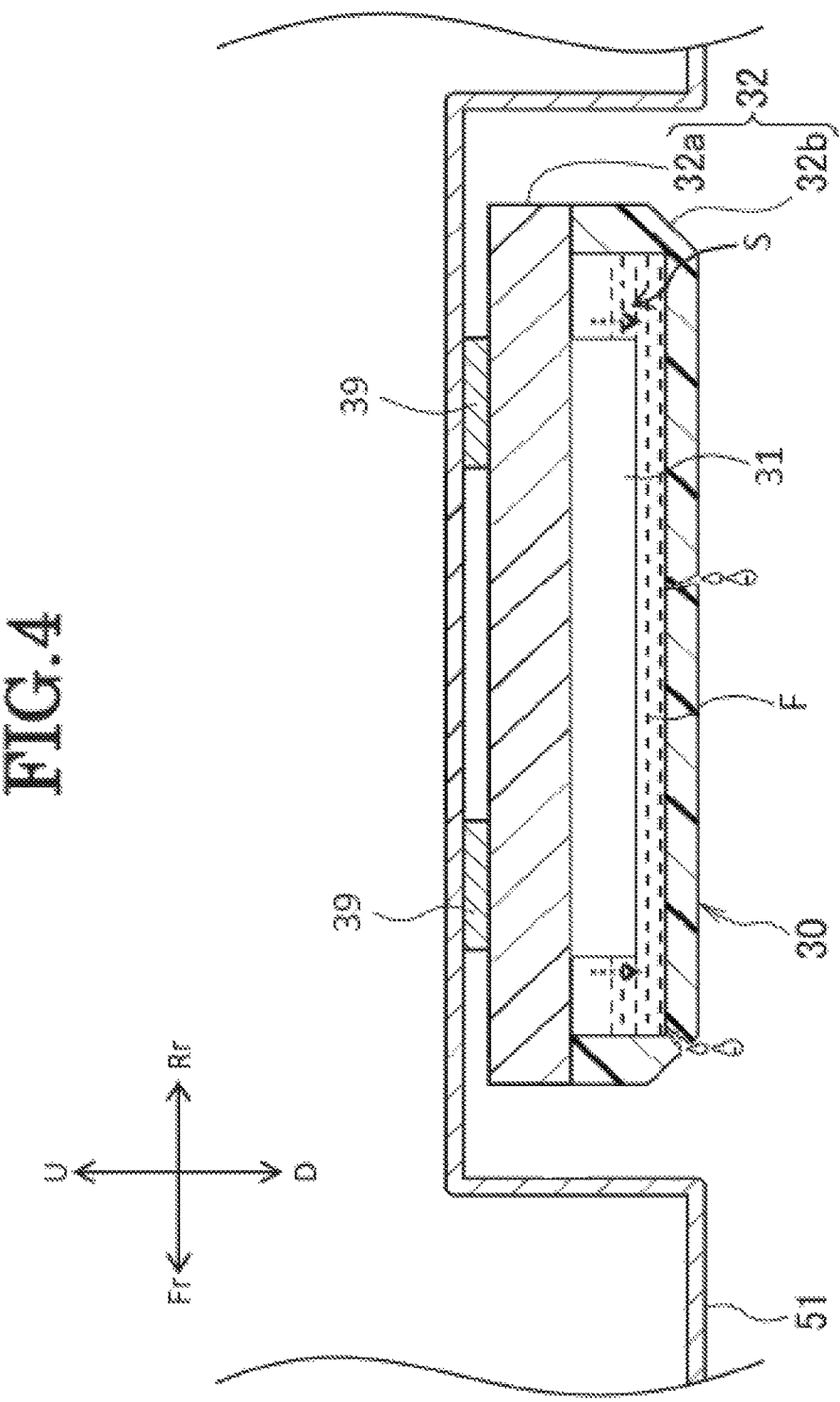
FIG. 4 is a sectional view of the power reception apparatus as seen from the side thereof, showing a state where a resin cover is damaged whereby a fluid level is lowered.
Figure 5:
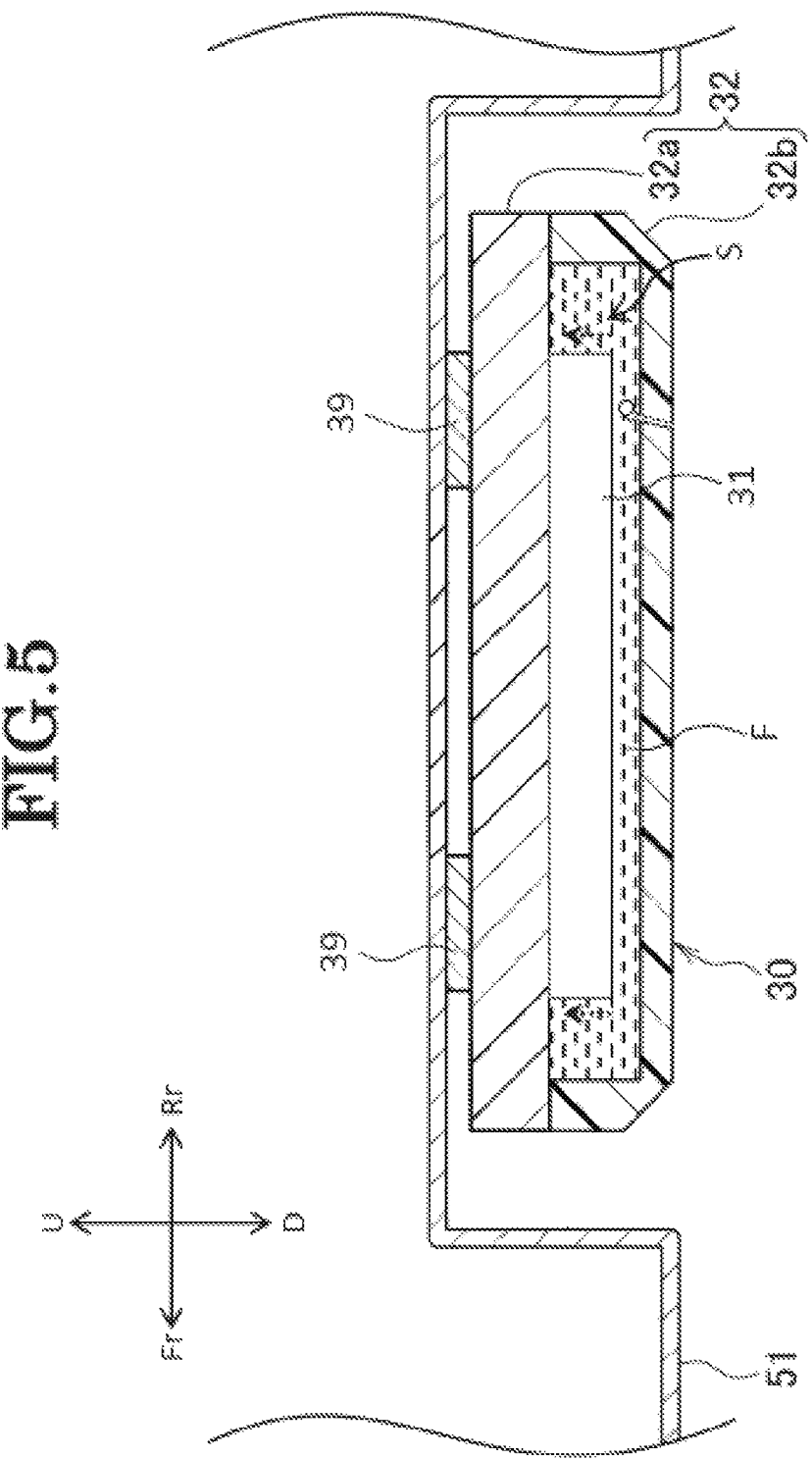
FIG. 5 is a sectional view of the power reception apparatus as seen from the side thereof showing a state where a crack is generated in the resin cover whereby a fluid level is raised.

The detection unit 37 detects damage made particularly to the resin cover 32b of the housing 32 according to the results of the measurement by the measurement unit 34. Since the power reception apparatus 30 is disposed at the bottom portion of the vehicle V, there is a risk of the resin cover 32b being damaged by a collision thereof with a projecting object provided on a road surface. When the resin cover 32b is damaged, the insulating fluid F which is filled in the space S leaks from a damaged portion, resulting in a case where a fluid level is lowered as indicated by arrows shown by dotted lines in FIG. 4. In the case where the damage made to the resin cover 32b is something like a crack, although no insulating fluid F leaks due to the viscosity thereof, bubbles of air enter the interior of the space S from the damaged-portion, resulting in a case where the fluid level is raised as indicated by arrows shown by dotted lines in FIG. 5. When the fluid level of the insulating fluid F changes, a magnetic permeability around the secondary coil 31 changes, whereby the power transmission efficiency and the coupling coefficient between the primary coil L and the secondary coil 31 are reduced. Consequently, the detection unit 37 determines whether or not the resin cover 32b of the housing 32 is damaged by following a flow chart shown in FIG. 6.

Figure 6:
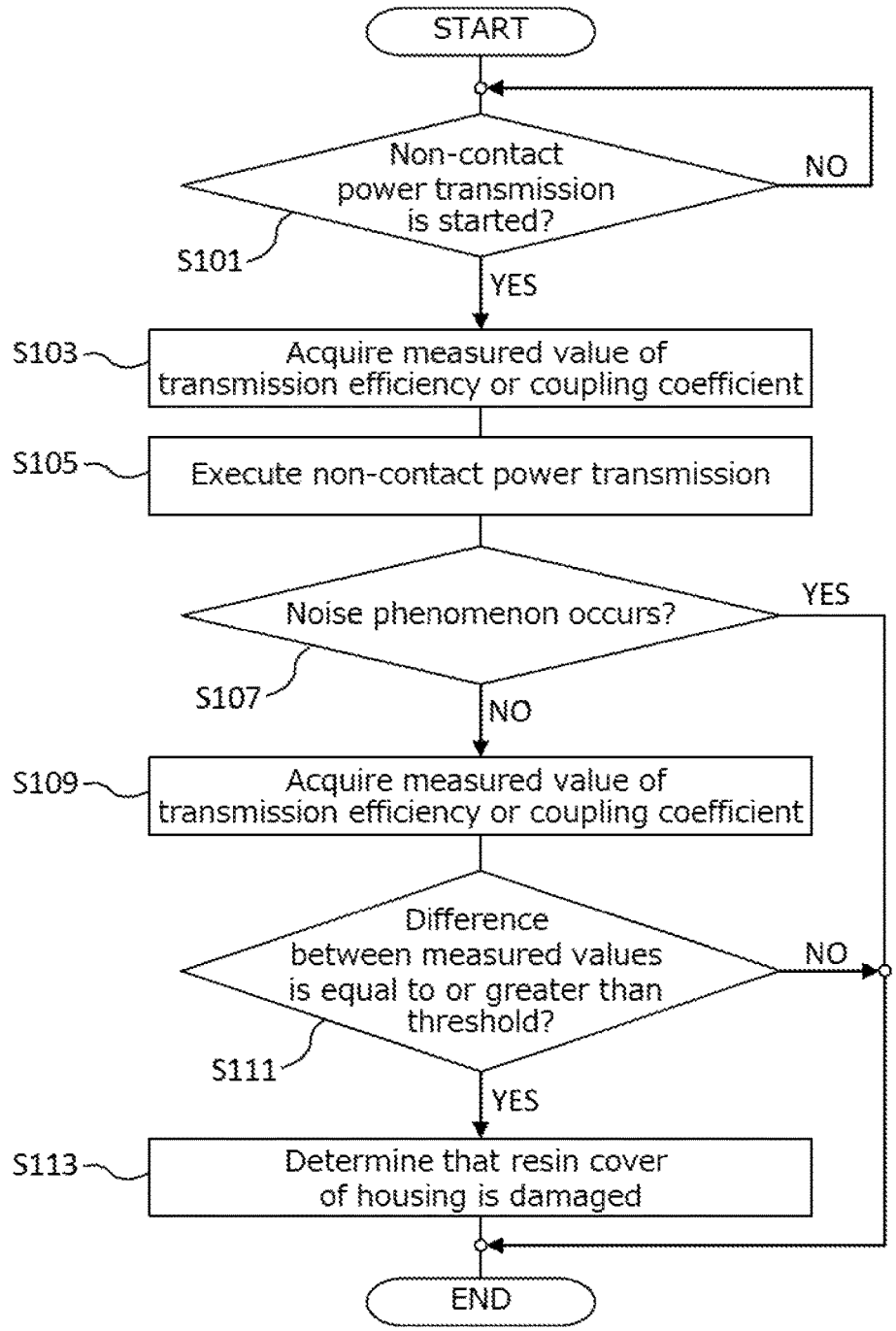
FIG. 6 is a flowchart showing an operation of a detection unit.

The operation of the detection unit 37 which follows the flow chart shown in FIG. 6 will be described. The detection unit 37 determines whether or not a non-contact power transmission from the power transmission apparatus T to the power reception apparatus 30 is started (step S101), and if the detection unit 37 determines that the non-contact power transmission is to be started, the flow of operations proceeds to step S103. In step S103, the detection unit 37 instructs the measurement unit 34 to measure the power transmission efficiency or the coupling coefficient described above and acquires a measured value. Next, the detection unit 37 executes the non-contact power transmission (step S105).

Next, the detection unit 37 determines whether or not a phenomenon which constitutes noise to the power transmission efficiency or the coupling coefficient (hereinafter, referred to as a "noise phenomenon") occurs during the non-contact power transmission (step S107). The noise phenomenon is, for example, an impact to the power reception apparatus 30 that is given when a door of the vehicle V is opened or closed and a power change of an exterior power system to which the primary coil L of the power transmission apparatus T is connected. When an acceleration sensor 38 that is provided on the power reception apparatus 30 detects an impact to the power reception apparatus 30, the detection unit 37 determines that the noise phenomenon has occurred. Additionally when a notice that a power change is generated in the exterior power system is sent from the power transmission apparatus T by way of the communication unit 33, the detection unit 37 determines that the noise phenomenon has occurred. The power change of the exterior power system includes, for example, a frequency change and a voltage drop, and when they are actually caused, the impedance matching is deteriorated and the amount of power transmitted is reduced, whereby the efficiency of the non-contact power transmission is badly affected.

When determining in step S107 that the noise phenomenon has occurred, the detection unit 37 ends the series of operations, whereas if determining that no noise phenomenon has occurred, the flow of operations proceeds to step S109. In step S109, as did in step S103, the detection unit 37 instructs the measurement unit 34 to measure an power transmission efficiency or a coupling coefficient and then acquires a measured value. Next, the detection unit 37 determines whether or not a difference between the measured value acquired in step S103 and the measured value acquired in step S109 is equal to or greater than a threshold (step S111). If the detection unit 37 determines that the difference is equal to or greater than the threshold, the flow of operations proceeds to step S113, whereas if the difference is less than the threshold, the detection unit 37 ends the series of operations. In step S113, the detection unit 37 determines that the resin cover 32b of the housing 32 is damaged.

When the detection unit 37 detects the damage of the resin cover 32b of the housing 32, the detection unit 37 sends a command to stop the transmission of power to the secondary coil 31 to the power transmission apparatus T by way of the communication unit 33. Upon receiving the command, the power transmission apparatus T stops the alternating current excitation of the primary coil L to ensure the safety.

Figure 7:
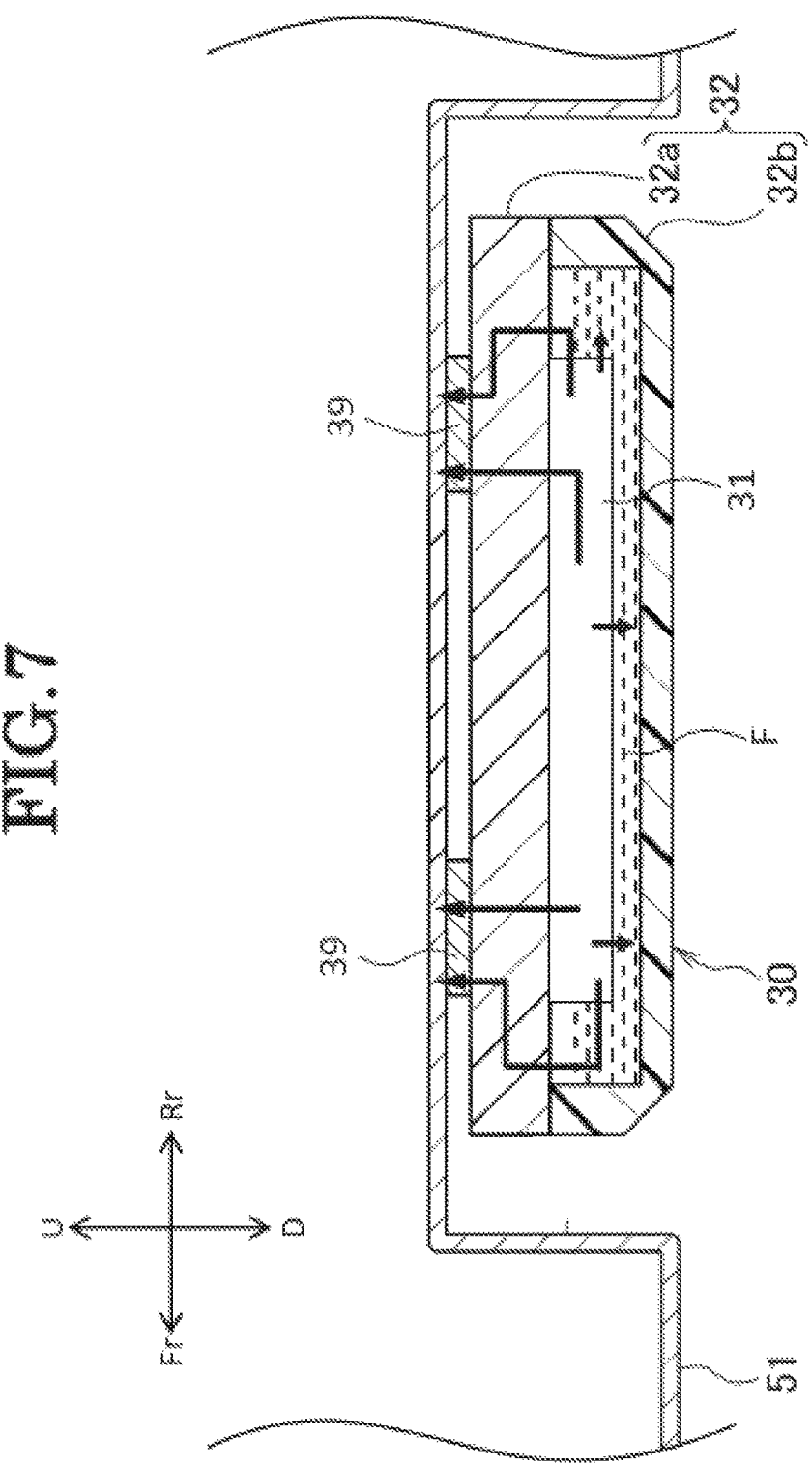
FIG. 7 is a schematic view showing a heat conduction path in the power reception apparatus.

The power reception apparatus 30 is disposed on a lower surface side of the bottom plate 51 of the battery case 50. A heat radiation sheet 39 is disposed on an upper surface of the housing 32 of the power reception apparatus 30. Heat generated in the secondary coil 31 which constitutes the main heat source of the power reception apparatus 30 is conducted directly to the base plate 32a whose heat conductivity is remarkably higher than those of the secondary coil 31 and the insulating fluid F or is conducted to the base plate 32a by way of the insulating fluid F that convects within the space S, as shown in FIG. 7. The heat conducted to the base plate 32a is conducted to the bottom plate 51 whose heat capacity is greater than that of the power reception apparatus 30 by way of the heat radiation sheet 39.

The rectifier includes a rectifying circuit that converts an inputted alternating current to a direct current for output, and an input side of the rectifier is connected to the power reception apparatus 30 and an output side thereof is connected to the junction box 27. By doing so, power received by the power reception apparatus 30 is inputted into the rectifier, where the alternating current is converted to a direct current, and thereafter, the battery modules 21 are charged with the converted direct current by way of the junction box 27.

Thus, as has been described heretofore, according to this embodiment, since the insulating fluid F is filled in the space S inside the housing 32 where the secondary coil 31 is accommodated, the secondary coil 31 can be cooled by the insulating fluid F that convects. When the resin cover 32b of the housing 32 is damaged, the insulating fluid F leaks from the damaged portion or bubbles of air enter the interior of the space S from the damaged portion, whereby the magnetic permeability around the secondary coil 31 changes to thereby change the efficiency of non-contact power transmission or the coupling coefficient between the primary coil L and the secondary coil 31. Since the power reception apparatus 30 of this embodiment has the measurement unit 34 for measuring the power transmission efficiency or the coupling coefficient, it is possible to detect damage to the resin cover 32b of the housing 32 from a change in the power transmission efficiency or the coupling coefficient. In this way, the cooling of the secondary coil 31 and the detection of the damage of the housing 32 can be realized at low costs by the simple and easy configuration.

In addition, in case an impact is given to the power reception apparatus 30 or there is a power change of the power system during the non-contact power transmission, the detection of damage of the housing 32 is not executed. Therefore, even when there is a power change transmission efficiency or coupling coefficient as a result of an impact being given to the power reception apparatus 30 or there being a power change of the power system, since the damage of the housing 32 is not erroneously detected, the accuracy with which the damage of the housing 32 is detected can be improved.

Additionally, since the heat conductivity of the base plate 32a which supports the secondary coil 31 is higher than that of the secondary coil 31, heat of the secondary coil 31 can be radiated to an exterior portion by way of the base plate 32a. Further, since the heat conductivity of the base plate 32a is higher than that of the insulating fluid F, heat conducted from the secondary coil 31 to the insulating fluid F can be radiated to an exterior portion by way of the base plate 32a.

When damage to the housing 32 is detected, the power transmission apparatus T is instructed to stop the transmission of power to the secondary coil 31, thereby making it possible to improve the safety of the power reception apparatus 30.

The invention is not limited to the embodiment that has been described heretofore and hence can be modified or improved as required.

DESCRIPTION OF REFERENCE NUMERALS AND CHARACTERS

2 Passenger compartment
3 Floor panel
10 Power supply device
20 Battery unit
21 Battery module
27 Junction box
30 Power reception apparatus
31 Secondary coil
32 Housing
32a Base plate
32b Resin cover
33 Communication unit
34 Measurement unit
35 Voltage sensor
36 Current sensor
37 Detection unit
38 Acceleration sensor
39 Heat radiation sheet
50 Battery case
51 Bottom plate
52 Cover
F Insulating fluid
L Primary coil
S Space
T Power transmission apparatus
V Vehicle

The invention claimed is:

1. A power reception apparatus, comprising:
a secondary coil which receives power in a non-contact state from a power transmission apparatus having a primary coil, while being disposed opposite to the power transmission apparatus;
a housing which accommodates the secondary coil to form a space between the secondary coil and the housing;
an insulating fluid filled in the space;
a measurement unit which measures efficiency of a non-contact power transmission between the primary coil and the secondary coil; and
a detection unit which detects damage made to the housing based on a change in the efficiency during the non-contact power transmission.

2. The power reception apparatus according to claim 1, comprising:
a sensor which detects an impact against the power reception apparatus,
wherein the detection unit detects damage made to the housing in a case that the sensor detects no impact during the non-contact power transmission, and a change in the efficiency during the non-contact power transmission is a reduction of a predetermined value or greater.

3. The power reception apparatus according to claim 1, comprising:
an acquisition unit which acquires information related to a power change of an exterior power system to which the primary coil is connected,
wherein the detection unit detects damage made to the housing in a case that the information does not indicate a power change of the power system during the non-contact power transmission, and a change in the efficiency during the non-contact power transmission is a reduction of a predetermined value or greater.

4. The power reception apparatus according to claim 1, comprising:
a sensor which detects an impact against the power reception apparatus; and
an acquisition unit which acquires information related to a power change of an exterior power system to which the primary coil is connected,
wherein the detection unit detects damage made to the housing in a case that the sensor detects no impact during the non-contact power transmission, the information does not indicate a power change of the power system during the non-contact power transmission, and a change in the efficiency during the non-contact power transmission is a reduction of a predetermined value or greater.

5. The power reception apparatus according to claim 1, wherein the housing includes a support portion which supports the secondary coil, and
the support portion has a higher heat conductivity than that of the secondary coil.

6. The power reception apparatus according claim 5, wherein the support portion has a higher heat conductivity than that of the insulating fluid.

7. The power reception apparatus according to claim 1, comprising:
a transmission unit which transmits a command to stop power transmission to the secondary coil in a case that the detection unit detects damage made to the housing.

8. A power reception apparatus, comprising:
a secondary coil which receives power in a non-contact state from a power transmission apparatus having a primary coil, while being disposed opposite to the power transmission apparatus;
a housing which accommodates the secondary coil to form a space between the secondary coil and the housing;
an insulating fluid filled in the space;
a measurement unit which measures a coupling coefficient between the primary coil and the secondary coil; and
a detection unit which detects damage made to the housing based on a change in the coupling coefficient between at a first time and at a second time that has elapsed from the first time.

9. The power reception apparatus according to claim 8, comprising:
a sensor which detects an impact against the power reception apparatus,
wherein the detection unit detects damage made to the housing in a case that the sensor detects no impact during the non-contact power transmission, and a change in the coupling coefficient during the non-contact power transmission is a reduction of a predetermined value or greater.

10. The power reception apparatus according to claim 8, comprising:
an acquisition unit which acquires information related to a power change of an exterior power system to which the primary coil is connected,
wherein the detection unit detects damage made to the housing in a case that the information does not indicate a power change of the power system during the non-contact power transmission, and a change in the coupling coefficient during the non-contact power transmission is a reduction of a predetermined value or greater.

11. The power reception apparatus according to claim 8, comprising:
a sensor which detects an impact against the power reception apparatus; and
an acquisition unit which acquires information related to a power change of an exterior power system to which the primary coil is connected,
wherein the detection unit detects damage made to the housing in a case that the sensor detects no impact during the non-contact power transmission, the information does not indicate a power change of the power system during the non-contact power transmission, and a change in the coupling coefficient during the non-contact power transmission is a reduction of a predetermined value or greater.

12. The power reception apparatus according to claim 8, wherein the housing includes a support portion which supports the secondary coil, and
the support portion has a higher heat conductivity than that of the secondary coil.

13. The power reception apparatus according claim 12, wherein the support portion has a higher heat conductivity than that of the insulating fluid.

14. The power reception apparatus according to claim 8, comprising:
a transmission unit which transmits a command to stop power transmission to the secondary coil in a case that the detection unit detects damage made to the housing.

15. A vehicle comprising a power reception apparatus, wherein the power reception apparatus comprises:
a secondary coil which receives power in a non-contact state from a power transmission apparatus having a primary coil, while being disposed opposite to the power transmission apparatus;
a housing which accommodates the secondary coil to form a space between the secondary coil and the housing;
an insulating fluid filled in the space;
a measurement unit which measures efficiency of a non-contact power transmission between the primary coil and the secondary coil; and
a detection unit which detects damage made to the housing based on a change in the efficiency during the non-contact power transmission.

16. A vehicle comprising a power reception apparatus, wherein the power reception apparatus comprises:
a secondary coil which receives power in a non-contact state from a power transmission apparatus having a primary coil, while being disposed opposite to the power transmission apparatus;
a housing which accommodates the secondary coil to form a space between the secondary coil and the housing;
an insulating fluid filled in the space;
a measurement unit which measures a coupling coefficient between the primary coil and the secondary coil; and
a detection unit which detects damage made to the housing based on a change in the coupling coefficient between at a first time and at a second time that has elapsed from the first time.

17. A detection method that is executed by a power reception apparatus comprising:
a secondary coil which receives power in a non-contact state from a power transmission apparatus having a primary coil, while being disposed opposite to the power transmission apparatus;
a housing which accommodates the secondary coil to form a space between the secondary coil and the housing; and
an insulating fluid filled in the space,
the method comprises the steps of:
measuring efficiency of a non-contact power transmission between the primary coil and the secondary coil; and
detecting damage made to the housing based on a change in the efficiency during the non-contact power transmission.

18. A detection method that is executed by a power reception apparatus comprising:
a secondary coil which receives power in a non-contact state from a power transmission apparatus having a primary coil, while being disposed opposite to the power transmission apparatus;
a housing which accommodates the secondary coil to form a space between the secondary coil and the housing; and
an insulating fluid filled in the space,
the method comprises the steps of:
measuring a coupling coefficient between the primary coil and the secondary coil; and
detecting damage made to the housing based on a change in the coupling coefficient between at a first time and at a second time that has elapsed from the first time.

* * * * *